United States Patent
Tanaka et al.

(10) Patent No.: US 9,216,140 B2
(45) Date of Patent: Dec. 22, 2015

(54) PROCESS FOR PRODUCING RESIN COMPOSITION AND PROCESS FOR PRODUCING MOLDED ARTICLE

(75) Inventors: Jiro Tanaka, Okayama (JP); Kazuomi Suzuki, Okayama (JP)

(73) Assignee: NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 718 days.

(21) Appl. No.: 13/208,884

(22) Filed: Aug. 12, 2011

(65) Prior Publication Data

US 2011/0300508 A1 Dec. 8, 2011

Related U.S. Application Data

(62) Division of application No. 12/656,500, filed on Feb. 1, 2010, which is a division of application No. 11/795,502, filed as application No. PCT/JP2006/300772 on Jan. 19, 2006, now abandoned.

(30) Foreign Application Priority Data

Jan. 20, 2005 (JP) ................................ 2005-013231

(51) Int. Cl.
*A61K 6/10* (2006.01)
*A61C 13/00* (2006.01)
*A61C 13/07* (2006.01)

(52) U.S. Cl.
CPC .............. *A61K 6/10* (2013.01); *A61C 13/0024* (2013.01); *A61C 13/0025* (2013.01)

(58) Field of Classification Search
CPC ......................... A61C 13/0024; A61C 13/0025
USPC ............ 264/16, 17; 433/168.1, 214; 522/908; 523/109
See application file for complete search history.

(56) References Cited

U.S. PATENT DOCUMENTS

| | | | |
|---|---|---|---|
| 2,861,973 A | | 11/1958 | Wechsler |
| 4,089,763 A | | 5/1978 | Dart et al. |
| 4,433,958 A | * | 2/1984 | Fellman et al. ............ 433/199.1 |
| 4,459,193 A | * | 7/1984 | Ratcliffe et al. .............. 522/24 |
| 5,037,473 A | * | 8/1991 | Antonucci et al. ............. 106/35 |
| 5,075,107 A | | 12/1991 | Katakura et al. |
| 5,401,806 A | * | 3/1995 | Braden et al. ................. 525/301 |
| 5,502,086 A | | 3/1996 | Hiratani et al. |
| 6,063,831 A | | 5/2000 | Kubo et al. |
| 6,136,886 A | | 10/2000 | Deguchi |
| 6,159,012 A | * | 12/2000 | Oxman et al. ............. 433/228.1 |
| 6,572,693 B1 | | 6/2003 | Wu et al. |
| 2002/0058727 A1 | | 5/2002 | Nakayama et al. |

FOREIGN PATENT DOCUMENTS

| | | |
|---|---|---|
| GB | 2347679 | 9/2000 |
| JP | 3-20204 A | 1/1991 |
| JP | 03-112911 A | 5/1991 |
| JP | 11-140128 A | 5/1999 |
| JP | 2000-254152 A | 9/2000 |
| JP | 2002-104913 A | 4/2002 |
| JP | 2004-043558 A | 2/2004 |

OTHER PUBLICATIONS

Billmeyer, Jr. F. Textbook of Polymer Science, 1984, 3rd edition, pp. 210-212.*
Mironets, "N.V. Comparative Sanitary—Toxicological Features of Plasticizers Vinyl Methyl Adipate and Divinyl Adipate and Their Standardization in Water Tanks", Gigiena I Sanitariya, 1970, vol. 35, No. 10, pp. 88-89, (abstract)CA[online]STN, AN.74:34456.
Andreopoulos et al., "Plasticization of Acrylic Resins Used in Dentistry", Journal of Materials Science Letters, 1984, vol. 3, No. 11, pp. 1029-1030.
Nakamura, "Phthalic Acid Ester Free no Nenmaku Choseizai no Kaihatsu o Mezashite", The Journal of the Japan Dental Association, 2003, vol. 56, No. 4, pp. 347-357.
Kawahara et al., "Non-Phthalate Ester Plasticizer o Gan'yu shita Karifuzai no Yoshutsu Tokusei", The Journal of the Japanese Society for Dental Materials and Devices, 2004, vol. 23, No. 2, p. 165.
Parker, "Soft Acrylic Resin Materials Containing a Polymerisable Plasticiser II: Water Absorption Characteristics", Biomaterials, 1999, vol. 20, No. 1, pp. 55-60.
Machine translation of Kusaka, JP 2004-043558 A, translated on Aug. 11, 2008.
"Divinyl adipate," Qingdao Wings International Co., Ltd., 2008, 51EV Limited, http://wingschem.51ev.com/group-Organic-Intermediate/362968/Adipic-acid-divinyl-ester.html.

* cited by examiner

*Primary Examiner* — Nicole M Buie-Hatcher
(74) *Attorney, Agent, or Firm* — Buchanan, Ingersoll & Rooney PC

(57) ABSTRACT

A medical resin composition is produced by mixing a powder of a polymer (A) comprising repeating units having an ester group and a liquid of a vinyl ester monomer (B) having 6 or more carbon atoms to increase a viscosity and, according to demand, further performing a polymerization reaction. The thus produced resin composition inhibits leaching of irritative substances, reduces any adverse effects on the human body by endocrine disruptors, etc. and can be prepared with high operational efficiency. The resin composition is suitably used as a dental resin composition such as a tissue conditioner, a functional impression material, a lining material, a denture base material or a mouth piece material.

6 Claims, 6 Drawing Sheets

PROCESS FOR PRODUCING RESIN COMPOSITION AND PROCESS FOR PRODUCING MOLDED ARTICLE

CROSS-REFERENCE TO RELATED APPLICATIONS

This application is a divisional of application Ser. No. 12/656,500, filed Feb. 1, 2010, the contents of which are incorporated herein by reference, which is a divisional of application Ser. No. 11/795,502, filed Jul. 18, 2007, the contents of which are incorporated herein by reference, which was the National Stage filing under §371 of PCT/JP2006/300772 filed Jan. 19, 2006, which in turn claims priority to Japanese Application No. 2005-013231, filed Jan. 20, 2005.

TECHNICAL FIELD

The present invention relates to medical resin compositions, especially dental resin compositions, comprising a polymer comprising repeating units having an ester group and a vinyl ester monomer. It relates also to processes for producing resin compositions and processes for producing molded articles.

BACKGROUND ART

Use of a denture for a long period of time will cause absorption of an alveolar ridge and fit between a mucosal surface of a denture and the mucosal surface in contact with the denture base gradually deteriorates. As a result, application of a local excess pressure to the mucosal surface in contact with the base develops an abnormal condition in the mucous membrane in contact with the denture base or the alveolar ridge. When the mucous membrane in contact with a denture base or the alveolar ridge has something wrong, it is recovered to a normal condition by lining the mucosal surface of the denture with a tissue conditioner or the like, which is a soft resin composition, to relax the pressure added to the mucosal surface in contact with the base from the denture at the time of occlusion.

Such a soft resin composition has a feature that during the use thereof the physical state changes from a paste form to a rubber form via a dough form, i.e., from a viscous fluid to an elastomer, by mixing a powder and a liquid. A mixture of the powder and the liquid is poured onto a mucosal surface of a denture while being in a viscous state and it is installed into an oral cavity while being in a fluid state to fill the gap between the mucosal surface of the denture and the mucosal surface in contact with the denture base. Then, the physical state changes with time to a viscoelastic material having no fluidity or to an elastomer. The soft resin composition which has changed to a viscoelastic material or an elastomer is usually held in the oral cavity in a state of being in contact with the mucosal surface in contact with the denture base usually for about 3 to about 10 days or, if long, for about 30 days.

In soft resin compositions now in the marketed, poly(alkyl (meth)acrylate) is widely used as a powder and mixtures of ethanol with a phthalic ester-based plasticizer typified by dibutyl phthalate (DBP), butyl butylphthalylglycolate (BPBG) and dibenzylbutyl phthalate are widely used as a liquid. Regarding the phthalic ester-based plasticizers, however, a possibility of affecting living bodies as endocrine disruptors has been pointed out and removal thereof has been desired. Ethanol, which is added for increasing a swelling speed of a poly(alkyl(meth)acrylate) when mixing a powder and a liquid, adversely gives stimulation to an oral cavity or leaches into saliva. Ethanol may also cause problems such as deterioration in physical properties of a denture base or deformation thereof because it exhibits swellability also to a denture base in contact.

Patent document 1 discloses a tissue conditioner comprising a mixture of a powder of a copolymer of butyl methacrylate and ethyl methacrylate or a mixture of poly(butyl methacrylate) and poly(ethyl methacrylate) and a liquid of an aromatic carboxylic acid ester such as phthalic ester. According to patent document 1, the tissue conditioner can eliminate displeased feeling of patients during its use caused by stimulation or odor because the tissue conditioner is free from ethanol. However, phthalates and the like are endocrine disruptors, and in other aromatic carboxylate, there are fears of effects on living bodies.

Patent document 2 discloses a soft resin composition for denture bases which comprises (meth)acrylate monomer, an acid ester-based plasticizer, a poly(alkyl(meth)acrylate) and a polymerization initiator. According to patent document 2, in the resin composition, when using an acid ester-based plasticizer instead of phthalic ester-based plasticizer, properties desired for a soft resin composition such as moderate softness and compatibility between a denture base and a mucous membrane in oral cavity can be satisfied without using endocrine disruptors. However, use of an acid ester-based plasticizer unfortunately leads to deterioration in workability due to a low swelling speed of a poly(alkyl(meth)acrylate). In some examples provided in patent document 2, ethanol is added. Further, because an acrylic monomer is used, stimulation by the monomer to an oral cavity often becomes a problem.

Patent document 3 discloses a resin material for a denture base comprising a mixture of a polymerizable monomer having an unsaturated double bond, a poly(alkyl(meth)acrylate) and a polymerization catalyst, wherein at least a part of the poly(alkyl(meth)acrylate) is dissolved in the polymerizable monomer. It is reported that this does not need operations of weighing a powder and a liquid, mixing and kneading them and leaving them at rest for a certain period of time and that the operations can be simplified because it is already in a paste form. It, however, is necessary to harden the material by use of heat, UV rays or the like and therefore it is often unsuitable for taking an impression in an oral cavity.

Patent document 4 discloses a dental plastic pattern material for the production of a cast metal dental clasp or a cast metal denture base, comprising a mixture of a plasticizer such as a vinyl acetate monomer and poly(methyl methacrylate) A plastic pattern having elasticity and restorability can be obtained with sufficient workability by conducting cure polymerization after attaching the pattern material in an unpolymerized or preliminarily polymerized state to a model of the portion to which a cast metal clasp or a cast metal denture base is to be mounted. In a working example, a process for producing a plastic pattern is disclosed, in which a pattern forming material prepared by mixing a vinyl acetate monomer with a powder of poly(methyl methacrylate) to form a paste is attached to a surface of a plaster model and then it is subjected to cure polymerization by heating. The pattern material disclosed in patent document 4 is not one which is installed into an oral cavity, but one which is cured while being attached to a model. For this reason, a highly volatile monomer, such as a vinyl acetate monomer, is preferably used in the pattern material. In a case of installation into an oral cavity, however, use of a volatile monomer is undesirable from the safety viewpoint.

Patent document 1: JP 3-20204 A
Patent document 2: JP 2002-104913 A

Patent document 3: JP 2000-254152 A
Patent document 4: JP 3-112911 A

DISCLOSURE OF THE INVENTION

Problem to be Solved by the Invention

The present invention was made in order to solve the above-mentioned problems. An object of the present invention is to provide a resin composition which inhibits leaching of irritative substances and reduces adverse effects on the human body caused by endocrine disruptors, etc. and can be prepared with high operational efficiency and which is suitable for medical applications.

Means for Solving the Problem

The above-mentioned problems are solved by providing a medical resin composition comprising a polymer (A) comprising repeating units having an ester group and a vinyl ester monomer (B) having 6 or more carbon atoms. Herein, it is desirable that the polymer (A) is a poly(alkyl(meth)acrylate) (A1), particularly comprises at least one substance selected from the group consisting of poly(methyl methacrylate), poly(ethyl methacrylate) and methyl methacrylate-ethyl methacrylate copolymers. It is desirable that the vinyl ester monomer (B) is a vinyl carboxylate monomer (B1) and that the vinyl ester monomer (B) has two or more vinyl groups in the molecule.

It is desirable that the resin composition comprises the vinyl ester monomer (B) in an amount of from 20 to 200 parts by weight based on 100 parts by weight of the polymer (A). It is also desirable that the resin composition further comprises a polymerization initiator (C). One preferable embodiment of the medical resin composition of the present invention is a dental resin composition, and specifically, it is suitably used as at least one material selected from the group consisting of a tissue conditioner, a functional impression material, a lining material, a denture base material or a mouth piece material.

A particularly preferable embodiment is a dental resin composition which serves as at least one material selected from the group consisting of a tissue conditioner, a functional impression material and a lining material and which is to be inserted into an oral cavity, wherein the dental resin composition comprises 100 parts by weight of a poly(alkyl (meth) acrylate) (A1) and from 20 to 200 parts by weight of a vinyl carboxylate monomer (B1) having 6 or more carbon atoms.

The above-mentioned problems are solved also by providing a process for producing a resin composition comprising mixing a powder of a polymer (A) comprising repeating units having an ester group and a liquid of a vinyl ester monomer (B) having 6 or more carbon atoms to increase a viscosity. Herein, it is desirable that the powder of the polymer (A) has an average particle diameter of from 2 to 200 μm. It is also desirable to further add and mix a polymerization initiator (C) to increase a viscosity. It is also desirable that in a spreading test comprising sandwiching 1 mL of a resin composition obtained by mixing between glass plates and applying a load of 100 g, where a diameter of the resin composition spread after completion of the test is 30 mm, the time from mixing of the components (A) and (B) to start of the load application is from 3 to 8 minutes.

A particularly preferable embodiment is a process for producing a dental resin composition which serves as at least one material selected from the group consisting of a tissue conditioner, a functional impression material and a lining material and which is to be inserted into an oral cavity, comprising mixing 100 parts by weight of a powder of a poly(alkyl (meth)acrylate) (A1) having an average particle diameter of from 2 to 200 μm and from 20 to 200 parts by weight of a liquid of a vinyl carboxylate monomer (B1) having 6 or more carbon atoms to increase a viscosity.

A process for producing a molded article comprising increasing a viscosity of a resin composition prepared by the aforementioned process and molding it after the increasing of a viscosity is also a preferable embodiment of the present invention. Here, it is desirable that when the molded article is immersed in water at 37° C., a Shore C hardness (H7) measured seven days after start of immersion is from 0.8 to 1.2 times of a Shore C hardness (H1) measured one day after start of immersion. It is also desirable to perform a polymerization reaction after molding.

Effect of the Invention

The resin composition of the present invention can be used safely for the human body, especially in an oral cavity, because it inhibits leaching of irritative substances and it reduces any adverse effects on the human body by endocrine disruptors, etc. Further, it exhibits a high operational efficiency because a rate of viscosity increase during mixing of a powder and a liquid can be set within a proper range. Moreover, it is also possible to perform a crosslinking reaction according to demand. It therefore is easy to further reduce leaching components from the resin composition and to obtain molded articles with moderate hardness.

BEST MODE FOR CARRYING OUT THE INVENTION

Figure 1:
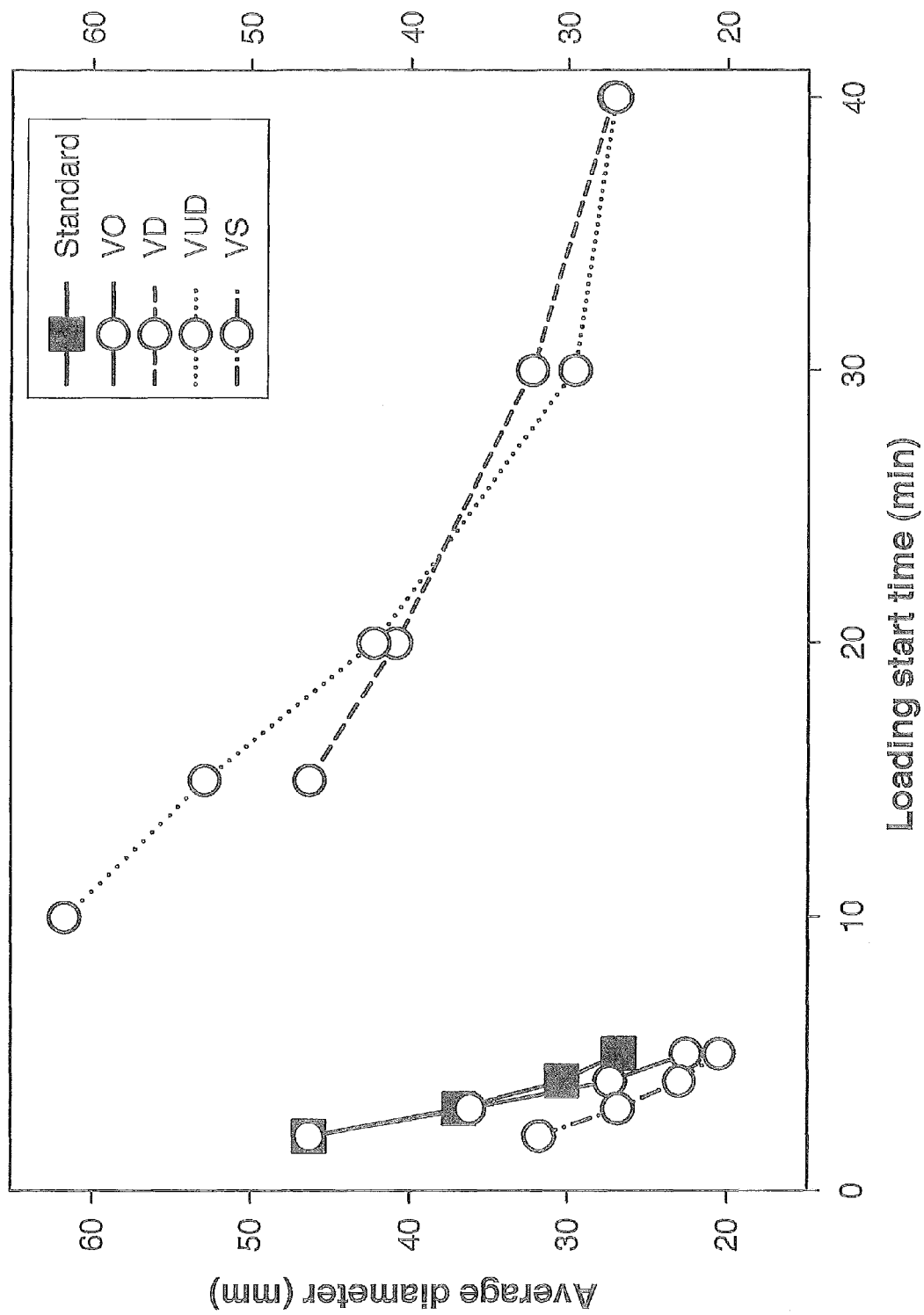
FIG. 1 A graph produced by plotting average diameters (mm) as ordinate against loading start times (min) as abscissa for examples using linear alkyl vinyl esters.

The resin composition of the present invention comprises a polymer (A) comprising repeating units having an ester group and a vinyl ester monomer (B) having 6 or more carbon atoms.

When the resin composition of the present invention is prepared by mixing a powder and a liquid, the physical state changes from a highly viscous liquid to a rubber form via a dough form, i.e., from a viscous fluid to an elastomer, by mixing the powder and the liquid. For example, in order to make the resin composition follow the shape of an oral cavity well, it is desirable to introduce it into the oral cavity while it is still in a highly viscous liquid where it retains fluidity thereof and make it change to an elastomer within a time which is not a burden on patients. It therefore is undesirable either that the above-described change of the state occurs too fast or that it occurs too slowly. Phthalic esters which have been used widely as a liquid make poly(methyl methacrylate), poly(ethyl methacrylate) or methyl methacrylate-ethyl methacrylate copolymers, which have been used as a powder, swell slowly and they therefore have needed use of ethanol in combination. Fatty acid ester type plasticizers have also been proposed. Their speeds of swelling polymers, however, have been insufficient as disclosed in comparative examples in the present specification.

The most important feature of the resin composition of the present invention is use of a vinyl ester monomer (B) having 6 or more carbon atoms as a compound to be mixed with a polymer (A) comprising repeating units having an ester group. The vinyl ester monomer (B) having 6 or more carbon atoms is often used as a polymerizable monomer. In the present invention, however, an attention is focused also on its performance as a plasticizer. Actually mixing it with a powder comprising poly(methyl methacrylate), poly(ethyl methacrylate) or a methyl methacrylate-ethyl methacrylate copolymer made it clear that it can swell the powder at a sufficiently high speed. It therefore is not necessary to incorporate ethanol though use of phthalic esters or aliphatic esters, which are conventional plasticizers, has needed to do so.

Conventionally, in medical resin compositions, especially dental material resin compositions, alkyl (meth)acrylates have been widely used as monomers for allowing a polymerization reaction to proceed in a resin composition. The main reason for this is that they have polymerization reactivities high enough. The advantage is that it is possible to obtain a resin composition containing only a small amount of residual monomer after the polymerization reaction. The high reactivity, however, sometimes causes problems regarding reaction heat or shrinkage during the reaction or problems regarding stimulation to living bodies. On the other hand, use of a vinyl ester monomer (B) having 6 or more carbon atoms makes it possible to cause a polymerization reaction to proceed at a fully practical level though it is true that the polymerization reactivity decreases. Moreover, poly(vinyl ester) has a lower Tg and is more flexible than poly(alkyl (meth)acrylate), and it therefore is also easy to produce a tough mold article through the polymerization reaction. Even if some unreacted residual monomers remain, it will not leach out so much and the leaching thereof is inhibited effectively by progress of a polymerization reaction. Further, it is a compound with high safety to living bodies.

Firstly, a polymer (A) is described. A polymer (A) comprises repeating units having an ester group. Here, the ester group contained in the repeating units may be contained either in a side chain such as poly(alkyl(meth)acrylates) (A1) and poly(vinyl esters) or in the main chain such as polyesters.

Among them, poly(alkyl(meth)acrylates) (A1) are particularly suitably used as a polymer (A). The poly(alkyl (meth) acrylates) (A1) are amorphous polymers having relatively high glass transition temperatures and powders having a particle size suitable for carrying out the present invention can be obtained easily by suspension polymerization. Among them, it is particularly desirable that the polymer (A) comprises at least one selected from the group consisting of poly(methyl methacrylate), polyethyl methacrylate) and methyl methacrylate-ethyl methacrylate copolymers. In this case, due to their high glass transition temperatures, molded articles with good shape retainability at near room temperature even after swelling tend to be formed. When a molded article with a higher hardness is desired to be obtained, use of poly(methyl methacrylate) is preferred. In view of a swelling speed, poly (ethyl methacrylate) or a methyl methacrylate-ethyl methacrylate copolymer is preferred.

Other examples of polymers suitably used as a polymer (A) include polyesters, especially aliphatic polyesters. Many aliphatic polyesters have biodegradability and therefore they are of good biocompatibility and can be suitably used as a medical resin material. Examples of such aliphatic polyesters include polylactic acid), polybutylene succinate) and polycaprolactone, which may have been copolymerized with other copolymerization components. Among them, polylactic acid) is preferred from the viewpoint of biodegradability and bio-affinity. When a powder comprising such an aliphatic polyester and a liquid comprising a vinyl ester monomer (B) are mixed, it is possible to increase a viscosity relatively fast.

Although the molecular weight of the polymer (A) is not particularly limited, ones having a weight average molecular weight of from about 5,000 to about 2,000,000 are typically used. When the molecular weight is too low, there is a possibility that shape retainability of a molded article obtained therefrom may be poor because the resin composition becomes too soft. The molecular weight is more preferably 50,000 or more and even more preferably 100,000 or more. On the other hand, when the molecular weight is too high, there is a possibility that the resin composition may be too hard. The molecular weight is more preferably 1,500,000 or less and even more preferably 1,000,000 or less. The weight average molecular weight may be measured using gel permeation chromatography (GPC).

The vinyl ester monomer (B) having 6 or more carbon atoms is not particularly restricted and vinyl carboxylate monomers (B1), vinyl phosphate monomers, vinyl sulfonate monomers, etc. may be used. Among these, vinyl carboxylate monomers (B1) or vinyl phosphate monomers are suitably used, and especially vinyl carboxylate monomers (B1) are preferred from the viewpoints such as safety and easiness of obtaining thereof.

As a vinyl carboxylate monomer (B1), monovinyl esters may be used, and ones having two or more vinyl groups in the molecule such as divinyl esters and trivinyl esters may also be used. Examples of vinyl carboxylate monomers (B1) include linear saturated alkyl vinyl esters such as vinyl butyrate (n=6), vinyl caproate (n=8), vinyl caprylate (n=10), vinyl caprate (n=12), vinyl laurate (n=14), vinyl myristate (n=16), vinyl palmitate (n=18) and vinyl stearate (n=20); linear unsaturated alkyl vinyl esters such as vinyl undecylenate (n=13) and vinyl sorbate (n=8); branched alkyl vinyl esters such as vinyl isobutyrate (n=6), vinyl 2-methylbutyrate (n=7), vinyl isovalerate (n=7), vinyl pivalate (n=7), vinyl 2,2-dimethylbutanoate (n=8), vinyl 2-ethyl-2-methylbutanoate (n=9), vinyl 2,2-dimethylpentanoate (n=9), vinyl 2-ethylhexanoate (n=10), vinyl neononanoate (n=11) and vinyl neodecanoate (n=12); cycloalkyl vinyl esters such as vinyl cyclohexanecarboxylate (n=9); aromatic vinyl esters such as vinyl benzoate (n=9), vinyl p-methylbenzoate (n=10), vinyl cinnamate (n=11) and vinyl 4-tert-butylbenzoate (n=13); halogenated alkyl vinyl esters; alkyl vinyl dicarboxylates such as methyl vinyl sebacate (n=13). Examples of divinyl esters of carboxylic acids include divinyl oxalate (n=6), divinyl malonate (n=7), divinyl succinate (n=8), divinyl glutarate (n=9), divinyl adipate (n=10), divinyl azelate (n=11), divinyl suberate (n=12), divinyl sebacate (n=14), divinyl maleate (n=8), divinyl fumarate (n=8), divinyl phthalate (n=12), divinyl isophthalate (n=12) and divinyl terephthalate (n=12). Examples of trivinyl esters of carboxylic acids include trivinyl hemimellitate (n=15), trivinyl trimellitate (n=15) and trivinyl trimesate (n=15). The numbers in parentheses are the numbers of carbon atoms contained in the vinyl ester monomers (B).

The number of carbon atoms in a vinyl ester monomer (B) used in the present invention is 6 or more. It is undesirable that the vinyl ester monomer (B) has high volatility because odor will generated therefrom or it will leach out easily. It is undesirable also from the viewpoint of dimensional accuracy because great shrinkage will easily occur when a polymerization reaction is allowed to proceed. Generally, poly(vinyl esters) have glass transition temperatures lower than those of poly(alkyl(meth)acrylates). Especially, many poly(vinyl esters) resulting from polymerization of aliphatic vinyl ester monomers (B) having a large number of carbon atoms have glass transition temperatures not higher than room temperature. Therefore, when a polymerization reaction of the vinyl ester monomer (B) is allowed to proceed in the resin composition of the present invention, it is possible to inhibit the increase of a hardness by using the monomer (B) having an increased number of carbon atoms. In such a case, it is possible to obtain a molded article which is soft but exhibits a low leachability. The number of carbon atoms is more preferably 8 or more, and even more preferably 10 or more. On the other hand, if the number of carbon atoms is too large, a swelling speed decreases when a powder comprising a polymer (A) and a liquid comprising the vinyl ester monomer (B) are mixed. Therefore, the number of carbon atoms of the vinyl ester monomer (B) is preferably not more than 20, and more preferably not more than 15.

It is desirable that the vinyl ester monomer (B) has two or more vinyl groups in the molecule. By having a plurality of functional groups in the molecule, even the vinyl ester monomer (B) having a large molecular weight provides a high swelling speed when a powder comprising a polymer (A) and a liquid comprising the vinyl ester monomer (B) are mixed. Even a vinyl ester having a large molecular weight can be used with good operativity. As a result, a resin composition in which stimulation and leachability are inhibited can be obtained. Further, it is possible to polymerize the vinyl ester monomer (B) into a network form. Therefore, when allowing a polymerization reaction to proceed, it is possible to inhibit leachability greatly even when a polymerization ratio is not very high.

Taking the possibility of occurrence of adverse effects to living bodies such as endocrine disruption, it is desirable that the vinyl ester monomer (B) has a structure having no aromatic rings. Therefore, aliphatic vinyl esters, alicyclic vinyl ester and the like are suitably used. Taking the flexibility of a resulting resin composition into consideration, it is preferable to use an aliphatic vinyl ester. The aliphatic vinyl ester may be either a linear alkyl vinyl ester or a branched alkyl vinyl ester. It also may be either a monovinyl ester or a vinyl ester having two or more vinyl groups in the molecule.

A single kind of a vinyl ester monomer (B) may be used; or alternatively two or more kinds of vinyl ester monomers (B) may be used in combination. For example, it is permitted to use a monovinyl ester and a vinyl ester having two or more vinyl groups in the molecule in combination. It is also permitted to use a vinyl ester having few carbon atoms and a vinyl ester having many carbon atoms in combination. Moreover, it is also permitted to additionally use another kind of monomer copolymerizable with a vinyl ester monomer (B), e.g. a (meth)acrylate monomer, a styrene monomer and a vinyl chloride monomer, as far as the effect of the present invention is not inhibited. It is desirable not to use alcohol, such as ethanol, together because it will cause adverse effects due to its leaching out.

It is desirable that the resin composition of the present invention comprises the vinyl ester monomer (B) in an amount of from 20 to 200 parts by weight based on 100 parts by weight of the polymer (A). When the content of the vinyl ester monomer (B) is less than 20 parts by weight based on 100 parts by weight of the polymer (A), it may be impossible to plasticize the polymer (A) well and, therefore, it may be difficult to obtain fluidity sufficient, for example, for taking an impression of the oral cavity. The content is more preferably 30 parts by weight or more, and even more preferably 50 parts by weight or more. On the other hand, when the content of the vinyl ester monomer (B) is more than 200 parts by weight based on 100 parts by weight of the polymer (A), a viscosity of a resin composition after mixing may become too low or solidification may not proceed to a degree sufficient for maintaining the shape even after a lapse of long time. The content is more preferably 150 parts by weight or less, and even more preferably 120 parts by weight or less.

It is desirable that the resin composition of the present invention further comprises a polymerization initiator (C). This will make it possible, according to demand, to polymerize the vinyl ester monomer (B) effectively under mild conditions. The polymerization initiator (C) to be used is not particularly restricted if it can polymerize the vinyl ester monomer (B). For example, radical polymerization initiators and photopolymerization initiators are used. As radical polymerization initiators, organic peroxides and organic azo compounds are suitably used. Such a radical polymerization initiator may be either one which generates a radical when being heated or one which generates a radical at normal temperature when being mixed with an amine or the like. When using a photopolymerization initiator, a combination of a sensitizer and a reducing agent or the like is used.

When the polymerization initiator (C) is added, a desirable content thereof is from 0.01 to 10 parts by weight based on 100 parts by weight of a vinyl ester monomer (B). When the content is less than 0.01 parts by weight, an effect of promoting a polymerization reaction may become insufficient. The content is more desirably 0.1 parts by weight or more. On the other hand, when the content is more than 10 parts by weight, the effect of promoting a polymerization reaction will plateau and the amount of leaching components originating in the polymerization initiator (C) may increase. The addition amount is more desirably 5 parts by weight or less.

The resin composition of the present invention may include components other than the above-mentioned polymer (A), vinyl ester monomer (B) and polymerization initiator (C). For example, filler, colorant, antibacterial agents, flavor, etc. may be blended according to application.

A desirable process for producing the resin composition of the present invention is a process comprising mixing a powder of a polymer (A) comprising repeating units having an ester group and a liquid of a vinyl ester monomer (B) having 6 or more carbon atoms to increase a viscosity. When mixing the powder and the liquid, it is desirable in many cases to conduct stirring in order to enhance a rate of viscosity increase or to make the whole composition uniform. However, when it is desired to prevent air bubbles from coming into the resin composition, it may be desirable to disperse the powder into the liquid or impregnate the powder with the liquid and then leave them at rest without stirring to increase a viscosity.

It is desirable that a powder of the polymer (A) used herein has an average particle diameter of from 2 to 200 $\mu m$. When the average particle diameter is 2 $\mu m$ or less, it becomes difficult to handle it and also become difficult to produce it. The average particle diameter is more desirably 10 $\mu M$ or more. On the other hand, in a case where the average particle diameter is greater than 200 when a powder of the polymer (A) and a liquid of the vinyl ester monomer (B) are mixed, the workability may deteriorate due to decrease in a rate of viscosity increase or mechanical strength of a resulting resin composition may decrease. The average particle diameter is more desirably 100 μm or less.

By further adding and mixing a polymerization initiator (C) in addition to the polymer (A) and the vinyl ester monomer (B) to increase a viscosity, it is possible to perform a polymerization reaction effectively. In this case, it is desirable to mix the polymerization initiator (C) in advance with the polymer (A) or the vinyl ester monomer (B) because the operation can be simplified. It is preferable to mix the polymerization initiator (C) in advance with the vinyl ester monomer (B) because a liquid can be mixed uniformly more easily. When the polymerization initiator (C) is one which generates a radical by mixing two or more kinds of compounds, it is also permitted to mix one of them with the polymer (A) and another one with the vinyl ester monomer (B) in advance.

When mixing a powder of the polymer (A) and a liquid of the vinyl ester monomer (B) together, the vinyl ester monomer (B) permeates into the polymer (A) to swell the polymer (A). As a result, a viscosity increases gradually. It is desirable to increase a viscosity of the mixture in such a manner and then produce a molded article by molding it. The resin composition at the time of molding is desirably in a state where it retains its fluidity although its viscosity has fully increased. Molding is conducted by pressing against the mold or filling into a mold.

In a case of use in a medical application, the term "mold" as referred to herein is often the human body or a part thereof or a mold produced by transferring them.

The resin composition of the present invention further increases in viscosity after being molded and in many cases it substantially loses its fluidity to become a material having properties mainly of an elastomer. It may be used while being in this state. Alternatively, the vinyl ester monomer (B) contained therein may thereafter be polymerized. In a case of using a polymerization initiator (C) such as that makes a polymerization reaction proceed at room temperature, even only mixing causes a polymerization reaction to proceed simultaneously with increase in viscosity. However, when a polymerization reaction is caused to proceed by use of heat or light, the polymerization reaction substantially does not proceed, in many cases, before a treatment with heat or light.

As mentioned above, a resin composition obtained by mixing a powder of the polymer (A) and a liquid of the vinyl ester monomer (B) is increased in viscosity after mixing and then is molded. Also after molding, the resin composition is further increased in viscosity to substantially lose its fluidity. Therefore, for example when installing into an oral cavity and molding, it is desirable that the resin composition reaches a proper viscosity within a certain period of time in view of doctor's workability and burden to patients. A method of judging such a rate of viscosity increase is a spreading test. It is desirable that in a spreading test comprising sandwiching 1 mL of a resin composition obtained by mixing between glass plates and applying a load of 100 g, where a diameter of the resin composition spread after completion of the test is 30 mm, the time from mixing of the components (A) and (B) to start of the load application is from 3 to 8 minutes. When the time is shorter than 3 minutes, the rate of viscosity increase is so fast that it may be impossible to secure an operation time long enough. On the other hand, when the time is longer than 8 minutes, the rate of viscosity increase is so slow that operation efficiency decreases and a heavy burden is placed on patients. A concrete procedure of the spreading test is as disclosed in the following example section.

As described above, the resin composition of the present invention does not need incorporation of ethanol, which is necessary in use of phthalic esters or aliphatic esters, which are conventional plasticizers. In molded articles made of conventional resin compositions containing ethanol, increase in hardness which appears to be cause by leaching of ethanol into water is recognized. However, such increase in hardness is not recognized in a molded article of the present invention using a vinyl ester monomer (B). As a result, it is shown that the molded article exhibits low leachability. Accordingly, it is desirable that when the molded article is immersed in water at 37° C., a Shore C hardness (H7) measured seven days after start of immersion is from 0.8 to 1.2 times a Shore C hardness (H1) measured one day after start of immersion. Immediately after the start of the immersion, an initial change of a hardness occurs due to temperature change or water absorption change. Therefore, using a Shore C hardness (H1) measured one day after start of immersion as a standard, a hardness change occurring thereafter is judged. A concrete procedure of immersion into water is as disclosed in the following example section.

After conducting molding in a manner described above, it is also possible to cause a polymerization reaction to proceed. By doing so, it is possible to effectively inhibit leaching of a vinyl ester monomer (B) remaining in the molded article. Since it is also possible to increase a hardness of the resin composition by adjusting a kind of the vinyl ester monomer (B) and a degree of polymerization thereof, it is possible to obtain a molded article having a desired hardness easily and it is also possible to obtain resin compositions having any hardness depending on applications from soft resin compositions to hard resin compositions. By heating or applying light, it is possible to cause a polymerization reaction to proceed after molding. The method by heating is preferred in view of workability. For example, it is possible to cause a polymerization reaction to proceed easily by only immersing in hot water. Under some heating conditions, it is possible to cause a polymerization reaction to proceed without using a polymerization initiator (C).

The resin composition of the present invention explained above exhibits low leachability and has high safety to living bodies. It therefore can be used suitably as a medical resin composition. It is particularly suitable as a dental resin composition because it gives less stimulation when it comes into contact with a mucous membrane in an oral cavity and less substance is leached to saliva and also because it can be prepared with good operativity and can reduce burden to patients.

Specific examples of preferred embodiments when being used in dental applications include a tissue conditioner, a functional impression material, a lining material, a denture base material and a mouth piece material. Among these, a tissue conditioner, a functional impression material and a lining material have particularly great benefit of use of the resin composition of the present invention, because they are installed in an oral cavity while being in a highly viscous fluid state and changes into an elastomer whose fluidity has been lost almost completely within a predetermined period of time.

A tissue conditioner is a material used in order to recover a mucous membrane in contact with a denture base or alveolar ridge to a normal condition by relaxing a pressure added to the mucosal surface in contact with the denture base from the denture at the time of occlusion when application of a local excess pressure to the mucosal surface in contact with the base has developed an abnormal condition in the mucous membrane in contact with the denture base or the alveolar ridge. The resin composition of the present invention is a material which is poured on a mucosal surface of a denture while being in a highly viscous fluid state and then is installed into an oral cavity to fill the gap between the mucosal surface of the denture and the mucosal surface in contact with the denture base and change into an elastomer whose fluidity has been substantially lost within a predetermined period of time. Since it is required to change into an elastomer within an oral cavity of a patient, a resin composition having a high swelling speed is desired. It is desirable that the polymer (A) is poly (ethyl methacrylate) or a methyl methacrylate-ethyl methacrylate copolymer and that the number of carbon atoms in the vinyl ester monomer (B) is 15 or less. Since softness is required in the application, substantially no polymerization reaction of the vinyl ester monomer (B) is needed to proceed and, if any, a polymerization ratio may be low. It is also possible to convert it into a lining material by increasing a polymerization ratio.

A functional impression material is a material which is used for taking an impression after a denture is used for a certain period of time while being worn, in order to adjust improper fit of the denture during its actual use. A method of its installation into an oral cavity of a patient is similar to that of the above-mentioned tissue conditioner. However, the functional impression material must retain certain fluidity during its use and a swelling speed is not necessarily required to be as high as that of the tissue conditioner. Therefore, the number of carbon atoms in the vinyl ester monomer (B) is preferably not less than 8, and more preferably not less than 10. By use of an impression taken in such a way, the rear surface of a denture base is conditioned.

Necessity of causing a polymerization reaction to proceed is similar to that for the above-mentioned tissue conditioner. It is also possible to convert it into a lining material by increasing a polymerization ratio.

A lining material is an item which is attached to the rear surface of a denture base in order to correct an improper portion of a denture base. It is permissible that the resin composition of the present invention is installed into an oral cavity of a patient to take an impression by a method similar to those of a tissue conditioner or a functional impression material and then it is subjected to lining. Alternatively, it is also permissible to use a pattern prepared from an impression taken separately and line it with the resin composition of the present invention. A lining material is often used continuously for a term longer than the above-mentioned tissue conditioner or functional impression material, for example, for one month or more. For this reason, a lining material is desired to have good cushioning property as well as a certain level of strength. It therefore is in some cases desirable to cause a polymerization reaction to proceed a little. It is possible to adjust a hardness by adjusting a polymerization ratio.

In production of a denture base or a mouth piece, a molded article is produced, not very often, directly in an oral cavity using the resin composition of the present invention. In many cases, a molded article made of the resin composition of the present invention is produced by using an impression already taken. Since mechanical strength is required in these applications, it is desirable to cause a polymerization reaction to proceed after molding the resin composition of the present invention. The resin composition of the present invention can be used suitably also for such applications because of its excellent toughness.

Further, the resin composition of the present invention is considered to be suitable for use, for example, as bone cement in the orthopedics field because it has low leachability and high safety to living bodies and generates only a small amount of reaction heat or small shrinkage.

EXAMPLES

The present invention is described below with reference to examples. The measurements and evaluations disclosed in examples were carried out in the following methods.

(1) Average Particle Diameter

Measurement was repeated twice using a particle size analyzer, Microtrac HRA (based on the laser diffraction scattering method) produced by Nikkiso Co., Ltd., under conditions: sample amount of 0.1 g and measurement time of 20 seconds. The average of the measurements was used as the average particle diameter (μm) of a powder of the polymer (A).

(2) Spreading Test 2 g of a powder comprising a polymer (A) and 1.8 mL of a liquid were mixed and stirred for 30 seconds. Then, 1 mL of the mixture was poured into a jig for sampling. The jig for sampling was composed of a glass tube having an inner diameter of 10 mm and a silicone rubber piston. A plastic film for preventing adhesion was placed on the piston and then the mixture was poured thereon. The piston was pushed 30 seconds before a loading start time and thereby the mixture was extruded from the jig for sampling onto a glass plate (70 mm×70 mm×1 mm). The loading start time as referred to herein is a time from mixing of the powder and the liquid. When the loading start time had come, the mixture was pressed with a glass plate (70 mm×70 mm×1 mm) carrying a weight thereon and a load was thereby applied. In this operation, a load of 100 g, which is a combined weight of the weight and the glass plate, was applied. The load was thereafter applied for 30 seconds, and then the maximum diameter and the minimum diameter of the resin composition spread were measured. The average of the measurements was calculated as an average diameter (mm).

(3) Measurement of Rubber Hardness

A plastic film was placed on a glass plate and a ring mold having an inner diameter of 25 mm and a height of 10 mm was placed on the film. Next, 6 g of a powder comprising a polymer (A) and 5 mL of a liquid were mixed and stirred for 30 seconds. Then, the mixture was poured into the mold. Another plastic film was placed on the mold and further a glass plate was placed thereon. Two minutes after start of mixing, they were immersed in 37° C. water for 1 hour while sandwiching between the two glass plates. The sample taken out from the water was removed from the mold. The films were removed, and rubber hardness was measured (0 day). Then, the sample was immersed in 37° C. deionized water. One day later, three days later and seven days later, the sample was taken out from the deionized water and rubber hardness was measured. The rubber hardness (type C) was measured by a method in accordance with JIS K7312-1996 "Physical testing methods for molded products of thermoplastic polyurethane elastomers", Annex 2 "Type C test method of spring hardness test" using a durometer produced by KOBUNSHI KEIKI CO., LTD., "Asker durometer type C2."

Example 1

Spreading Test

A spreading test was conducted in accordance with the above-mentioned method by using 2 g of a powder of poly-ethyl methacrylate) (PEMA) having an average particle diameter of about 40 μm as a powder comprising polymer (A) and 1.8 mL of liquids comprising various vinyl ester monomers (B) shown below containing 1% by weight of benzoyl peroxide (C: polymerization initiator) as a liquid. A weight average molecular weight of the PEMA measured by gel permeation chromatography (GPC) is about 400,000. The mixture of dibutyl phthalate and 15% by weight of ethanol (Standard) corresponds to the recipe of tissue conditioners, which are commercially available at present. If the result of a spreading test is the same as or close to that of the mixture, it serves as a standard for judging that the operativity in use as a tissue conditioner is good.

[Linear Alkyl Vinyl Esters]
  Vinyl caprylate (VO: n=10: molecular weight 170.25)
  Vinyl caprate (VD: n=12: molecular weight 198.3)
[Branched Alkyl Vinyl Esters]
  Vinyl 2-methylbutyrate (V2 MB: n=7: molecular weight 128.17)
  Vinyl isovalerate (V3 MB: n=7: molecular weight 128.17)
  Vinyl pivalate (N5-VE: n=7: molecular weight 128.17)
  Vinyl 2,2-dimethylbutanoate (VDMB: n=8: molecular weight 142.2)
  Vinyl 2-ethyl-2-methylbutanoate (VEMB: n=9: molecular weight 156.22)
[Cycloalkyl Vinyl Ester]
  Vinyl cyclohexanecarboxylate (VCHC: n=9: molecular weight 154.21)
[Unsaturated Alkyl Vinyl Esters]
  Vinyl undecylenate (VUD: n=13: molecular weight 210.31)
  Vinyl sorbate (VS: n=8: molecular weight 138.16)
[Aromatic Vinyl Esters]
  Vinyl benzoate (VBz: n=9: molecular weight 148.16)
  Vinyl p-methylbenzoate (VMB: n=10: molecular weight 162.19)
  Vinyl cinnamate (VC: n=11: molecular weight 174.2)
  Vinyl 4-tert-butylbenzoate (VTBB: n=13: molecular weight 204.26)
[Alkyl Vinyl Dicarboxylate]
  Methyl vinyl sebacate (MVS: n=13: molecular weight 242.31)
[Divinyl Esters]
  Divinyl adipate (DVA: n=10: molecular weight 198.22)
  Divinyl sebacate (DVS: n=14: molecular weight 254.32)
[Other Liquids]
  Dibutyl adipate (DBA: n=14: molecular weight 258.4)
  Dibutyl sebacate (DBS: n=18: molecular weight 314.47)
  Mixture of dibutyl phthalate (n=16: molecular weight 278.35) and 15% by weight of ethanol (Standard)

Figure 2:
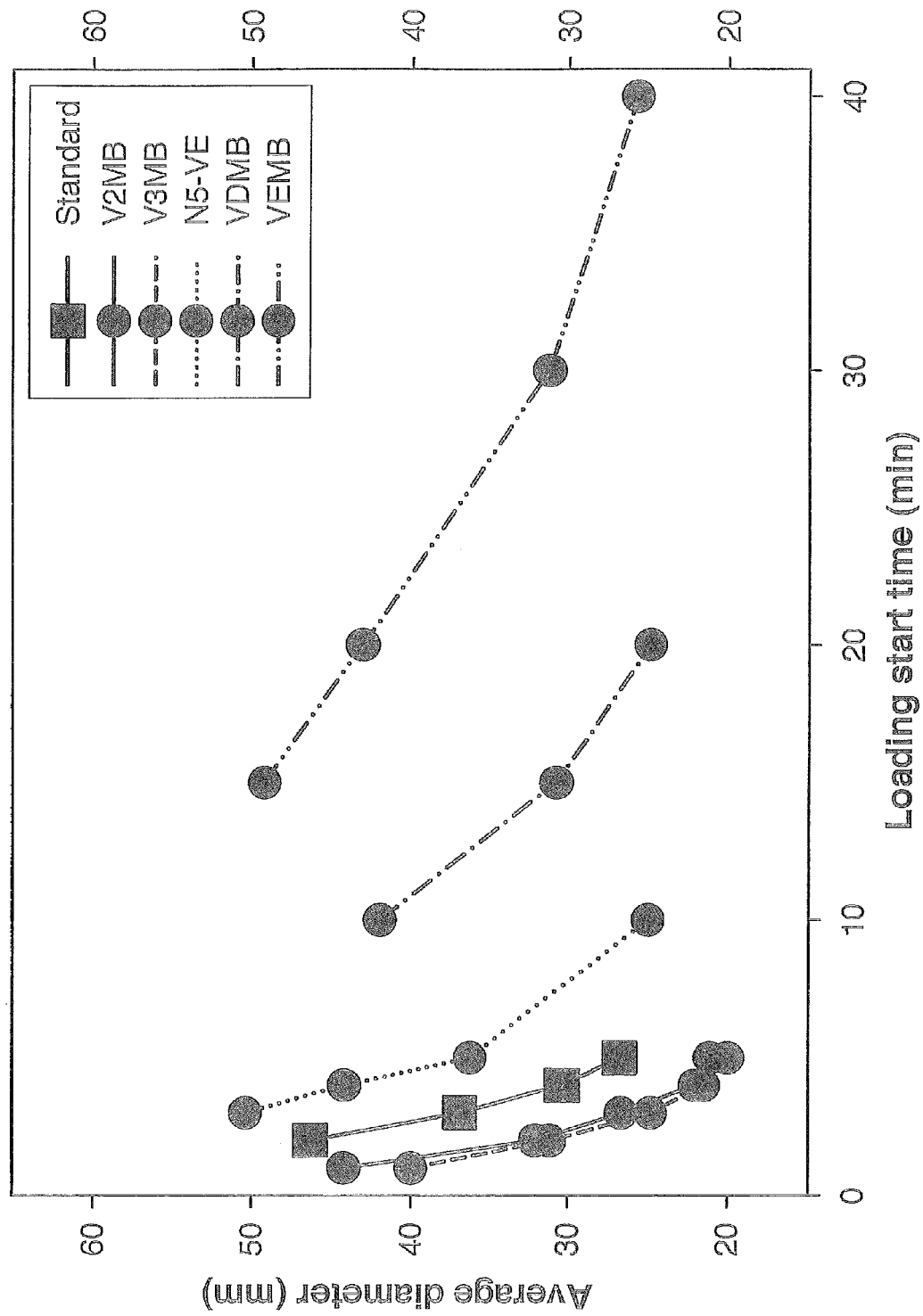
FIG. 2 A graph produced by plotting average diameters (mm) as ordinate against loading start times (min) as abscissa for examples using branched alkyl vinyl esters.
Figure 3:
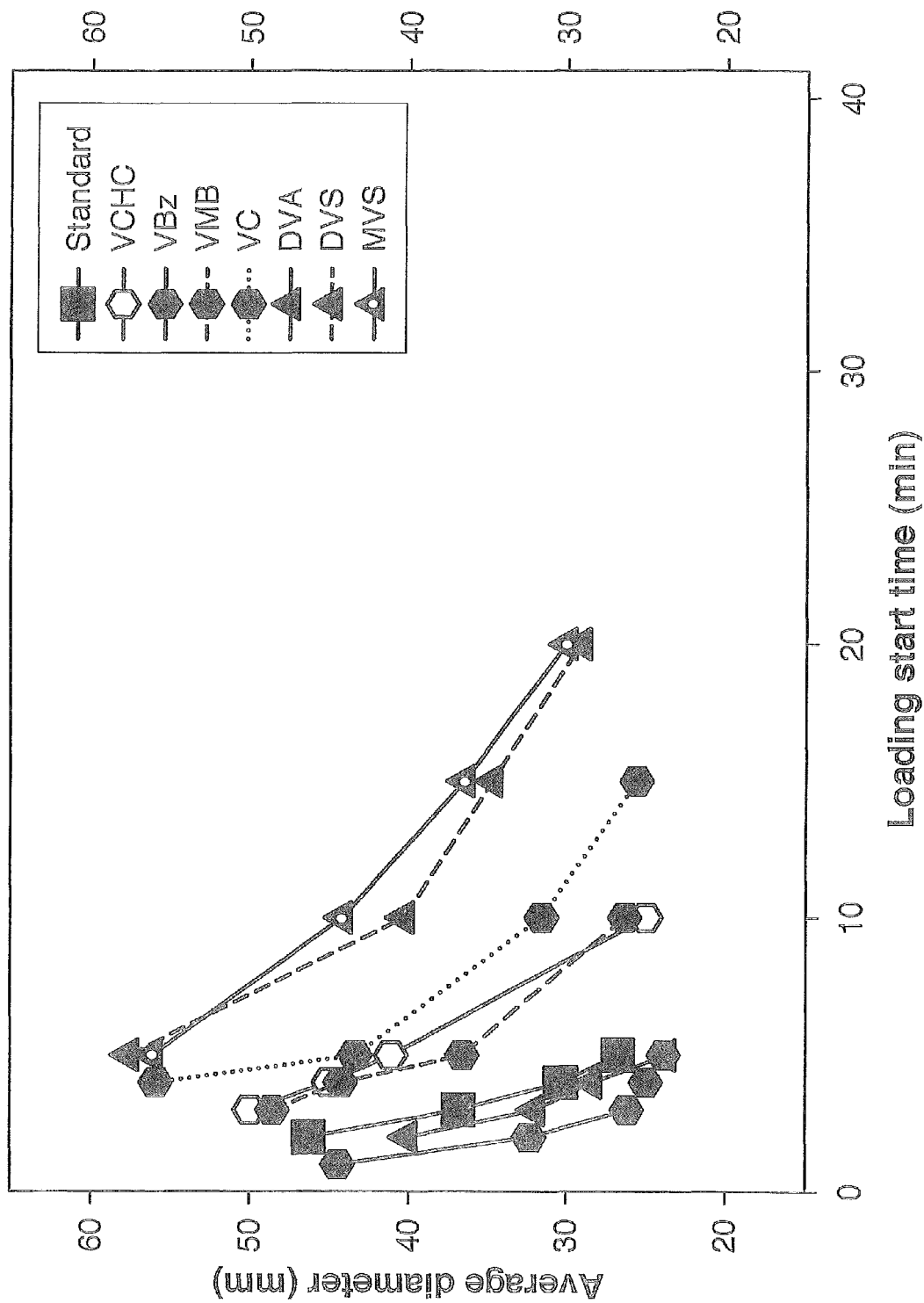
FIG. 3 A graph produced by plotting average diameters (mm) as ordinate against loading start times (min) as abscissa for examples using other vinyl esters.
Figure 4:
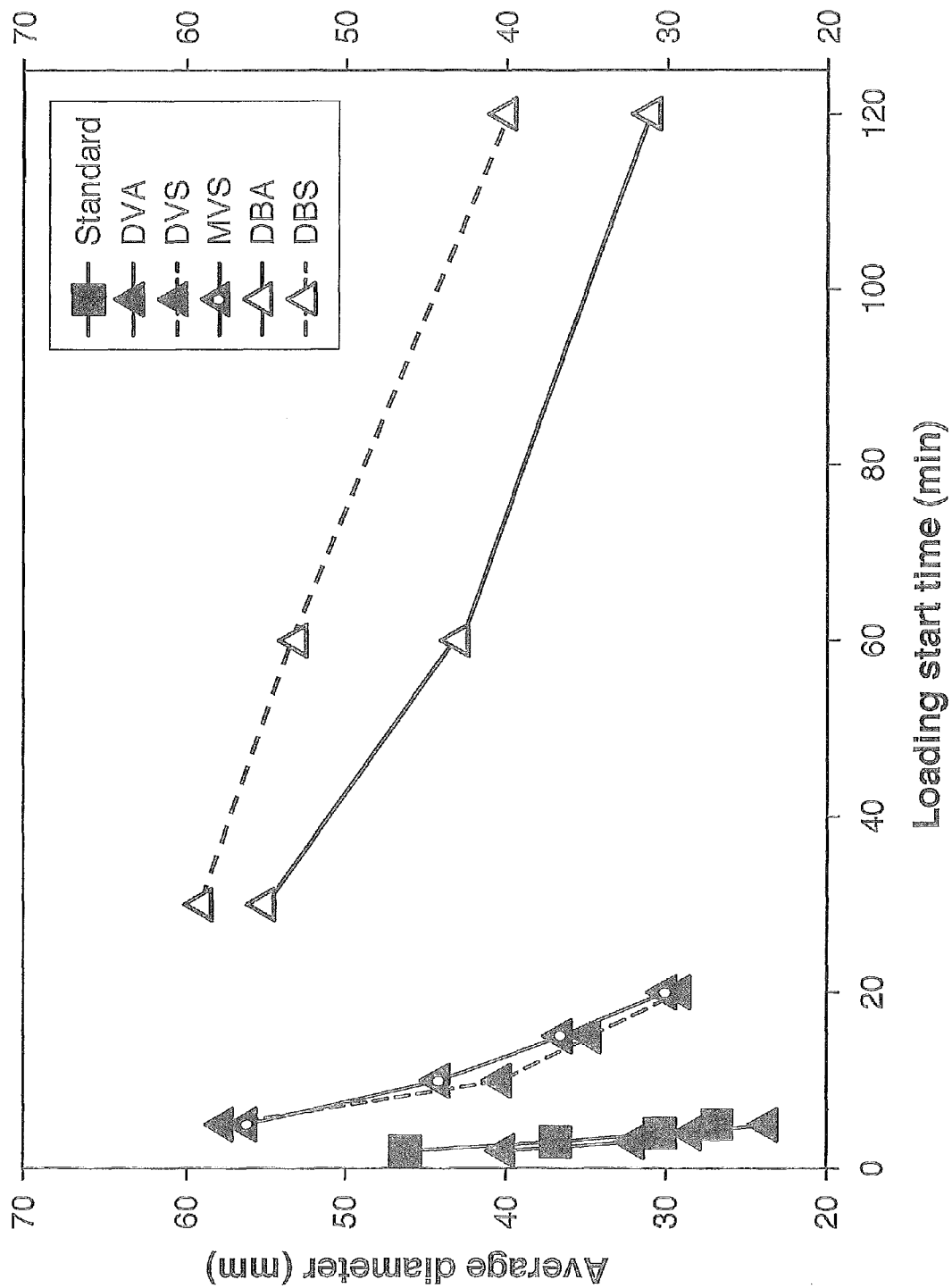
FIG. 4 A graph produced by plotting average diameters (mm) as ordinate against loading start times (min) as abscissa while comparing an example using divinyl esters, examples using alkyl vinyl dicarboxylates and examples using dialkyl aliphatic dicarboxylates.

Graphs produced by plotting average diameters (mm) as ordinate against loading start times (min) as abscissa are shown in FIGS. 1 to 4. FIG. 1 shows examples using linear alkyl vinyl esters; FIG. 2 shows examples using branched alkyl vinyl esters; and FIG. 3 shows examples using other types of vinyl esters. FIG. 4 shows comparison of examples using divinyl esters, an example using an alkyl vinyl dicarboxylate and examples using dialkyl aliphatic dicarboxylates. It is shown that the spreading rate can be controlled over a wide range by selecting a type of the vinyl ester monomer (B). In particular, vinyl caprylate (VO: molecular weight 170.25), which is a linear alkyl vinyl ester having 10 carbon atoms, and divinyl adipate (DVA molecular weight 198.22), which is a divinyl ester having 10 carbon atoms have spreading rates suitable for use as a tissue conditioner.

Figure 5:
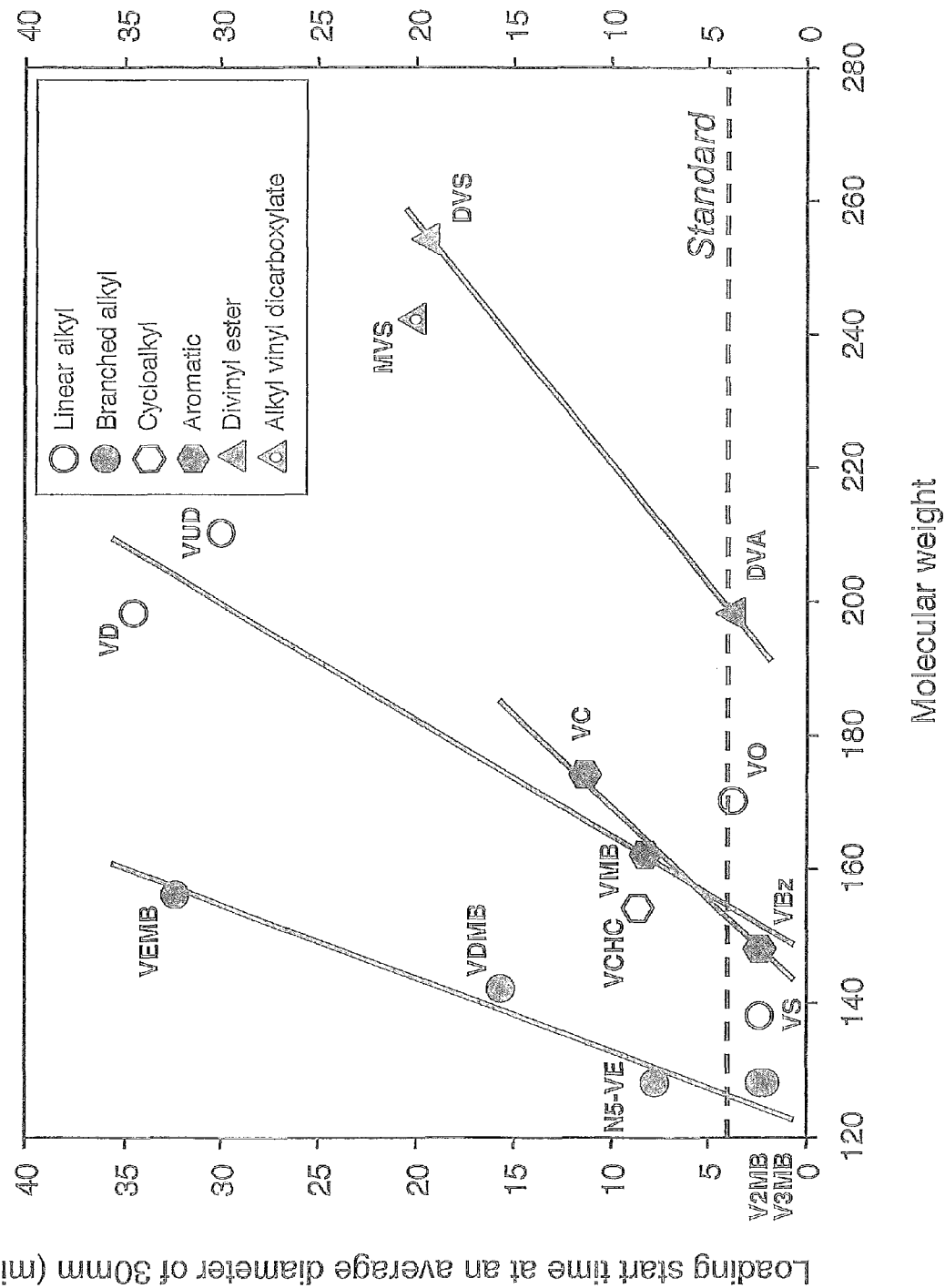
FIG. 5 A graph produced by plotting loading start times (min) at an average diameter of 30 mm as ordinate against molecular weights as abscissa.

Loading start times (min), which are expected to give an average diameter of 30 mm exactly in the graphs shown in FIGS. 1 to 4, were calculated. FIG. 5 is a graph produced by plotting loading start times (min) at an average diameter of 30 mm as ordinate against molecular weights of vinyl ester monomers (B) as abscissa, etc. Herein, the loading start time which results in an average diameter of 30 mm for "Standard", which is a mixture of dibutyl phthalate and ethanol, namely 4.1 minutes is shown by the dotted line parallel to the horizontal axis of the graph.

FIG. 5 shows that, for the same type of compounds, the higher the molecular weight is, the lower the rate of viscosity increase is. It is also shown that if the molecular weights are comparable, the rate of viscosity increase is greater in the order, linear alkyl vinyl esters (saturated and unsaturated) >cycloalkyl vinyl esters>branched alkyl vinyl esters. If the rate of viscosity increase is the same, the higher the molecular weight, the more advantageous from the viewpoint of volatility and leachability. From this point of view, one having a linear molecular skeleton is thought to be preferred. Aromatic vinyl esters provide relatively high rates of viscosity increase like linear alkyl vinyl esters, but it seems that they should be used with consideration for safety to living bodies such as endocrine disruption.

As shown in FIGS. 4 and 5, divinyl esters provide higher rates of viscosity increase than linear alkyl vinyl esters, provided that they are comparable with respect to molecular weight, and therefore divinyl esters are more advantageous from the viewpoint of volatility and leachability. When allowing a polymerization reaction to further proceed, it is possible to increase the leaching inhibition property to a higher degree because they have a plurality of polymerizable functional groups. It therefore is shown that divinyl esters are the most useful substances as the vinyl ester monomer (B) for use in the resin composition of the present invention. Alkyl vinyl dicarboxylates have only one vinyl ester group, but they have another ester group. Therefore, the rate of viscosity increase thereof is only a little slower than that of divinyl esters and it can be understood that they are also useful. In the case of dibutyl adipate (DBA: n=14: molecular weight 258.4), which only has two ester groups and has no vinyl groups, the rate of viscosity increase is greatly reduced though it has the same number of carbon atoms and almost the same molecular weight as those of divinyl sebacate (DVS: n=14: molecular weight 254.32). This shows that it is important, from the viewpoint of swellability, to have a vinyl ester group.

Example 2

Rubber Hardness Test

A Shore C hardness was measured in accordance with the above-mentioned method by using 6 g of a powder of poly (ethyl methacrylate) (PEMA) the same as that of Example 1 as a powder of polymer (A) and 5 mL of liquids comprising various vinyl ester monomers (B) shown below containing 1% by weight of benzoyl peroxide (C: polymerization initiator) as a liquid.

[Linear Alkyl Vinyl Ester]
  Vinyl caprylate (VO: n=10: molecular weight 170.25)
[Cycloalkyl Vinyl Ester]
  Vinyl cyclohexanecarboxylate (VCHC: n=9: molecular weight 154.21)
[Aromatic Vinyl Esters]
  Vinyl p-methylbenzoate (VMB: n=10: molecular weight 162.19)
  Vinyl cinnamate (VC: n=11: molecular weight 174.2)
[Divinyl Esters]
  Divinyl adipate (DVA: n=10: molecular weight 198.22)
[Other Liquids]
  Mixture of dibutyl phthalate (n=16: molecular weight 278.35) and 15% by weight of ethanol (Standard)

Figure 6:
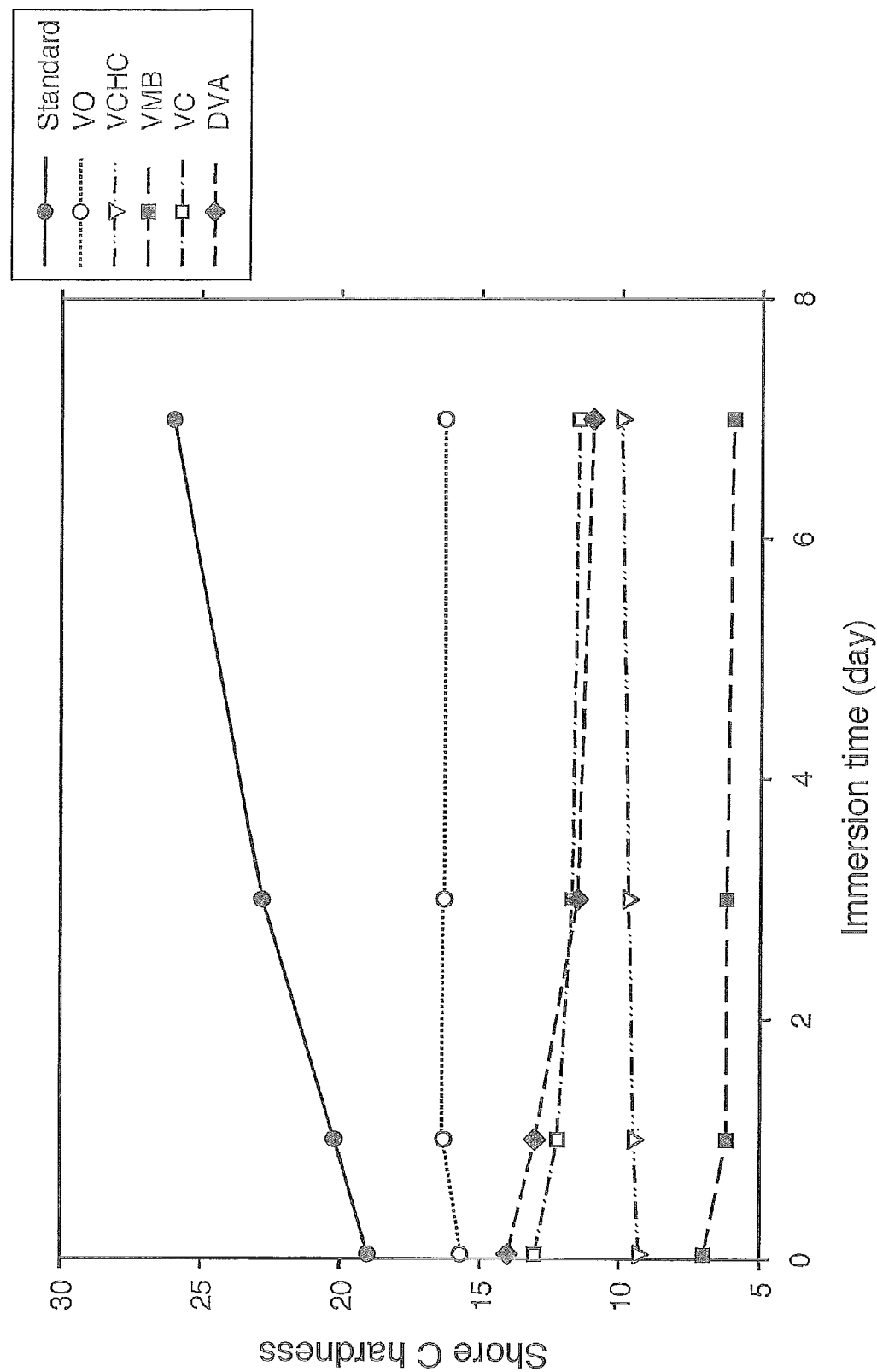
FIG. 6 A graph produced by plotting Shore C hardnesses as ordinate against immersion times (day) in water as abscissa.

FIG. 6 is a graph produced by plotting Shore C hardnesses as ordinate against immersion times (day) in water as abscissa. In the examples using a vinyl ester monomer (B), molded articles more flexible than "Standard" were obtained. It is also possible to further increase a hardness by polymerizing the vinyl ester monomer (B) afterward according to necessity. It therefore can be understood that it is possible to obtain molded articles with a wide range of rubber hardness, "Standard", which contains ethanol, exhibited increase in hardness which appears to be caused by leaching of ethanol into water. In the examples using the vinyl ester monomer (B), however, such increase in hardness was not recognized and it is shown that they are of low leachability.

Example 3

Polymerization Test 2 g of a powder of a methyl methacrylate (MMA: 40% by weight)-ethyl methacrylate (EMA: 60% by weight) copolymer having an average particle diameter of about 50 μm and 1 g of divinyl adipate (DVA) containing 1% by weight of benzoyl peroxide were mixed and then stirred for 30 seconds. A weight average molecular weight of the MMA-EMA copolymer measured by GPC was about 500,000. The resulting mixture was fed into a mold which can produce a specimen with dimensions 2 mm×2 mm×25 mm and was held at 100° C. for 10 min under a load of 3 ton. Thus, a polymerization reaction was allowed to proceed. After spontaneous cooling, the specimen taken out from the mold was left at rest in the air for one day and then was subjected to a three-point bending test (span: 20 mm, cross-head speed: 0.5 mm/min) with a universal testing machine (INSTRON 5544). Thus, flexural strength, flexural modulus, fracture energy and maximum deflection were measured. Further, samples before and after the polymerization reaction were subjected to absorption spectral measurement with a near infrared spectrometer. An amount of residual monomer was calculated from the height of absorption peaks due to terminal methylene groups and a polymerization ratio (%) was determined. In the same manner, samples obtained by using methyl methacrylate instead of divinyl adipate were also evaluated as comparative examples. The evaluation results are shown collectively in Table 1.

|  | MMA-EMA copolymer and DVA monomer | MMA-EMA copolymer and MMA monomer |
|---|---|---|
| Flexural strength (MPa) | 68.8 | 90.4 |
| Flexural modulus (GPa) | 1.91 | 2.63 |
| Fracture energy (kJ/m$^2$) | 22.22 | 7.78 |
| Maximum deflection (mm) | 6.45 | 2.16 |
| Polymerization ratio (%) | 77.2 | 99.3 |

A polymerization ratio in the case of using divinyl adipate (DVA), which is a vinyl ester monomer (B), is lower than that in the case of using methyl methacrylate (MMA) and it is shown that vinyl ester monomers (B) have reactivities lower than alkyl (meth)acrylates. Therefore, the flexural modulus and the flexural modulus were slightly lower than those in the case of using MMA. However, a fracture energy and maximum deflection in the case of using DVA are far greater than those in the case of using MMA and it therefore is shown that a molded article with excellent toughness was obtained. Such a molded article with excellent toughness can be used suitably as denture base materials or mouth piece materials if it is used in dental material applications.

Example 4

Use of Poly(Lactic Acid)

0.5 g of a powder of a lactic acid (75 mol %)-glycolic acid (25 mol %) copolymer ("PLGA-7510: molecular weight 10,000" produced by Wako Pure Chemical Industries, Ltd.), which is an aliphatic copolymerized polyester resin as a polymer (A), was charged into a mixing cup and 0.45 mL of vinyl propionate was added dropwise thereto. Stirring was continued for 30 seconds and physical condition change was observed. As a result, swelling (dissolution) proceeded at a speed almost the same as "Standard" and apparently homogeneous, a viscous liquid was formed in several minutes. However, even after a lapse of one night, it was still liquid with a further increased viscosity rather than rubber even though the viscosity had been increased. It had fluidity such that even if it is molded into a certain shape, the shape will be lost in one hour. When divinyl adipate (DVA) was used instead of vinyl propionate, the swelling (dissolution) speed was very slow and it took half a day to reach the same condition. It therefore was found that it is difficult to be used for applications where an elastomer should be formed only by mixing. It, however, must be possible to eliminate the fluidity by crosslinking. It is considered to be a material useful for applications where biodegradability is required.

The invention claimed is:

1. A process for producing a molded article suitable for use in a dental application, the process comprising:
   mixing 100 parts by weight of a powder of a polymer (A) comprising repeating units having an ester group and having a weight average molecular weight of from 5,000 to 2,000,000, and from 20 to 200 parts by weight of a liquid of a vinyl ester monomer (B) having 6 or more carbon atoms and having a plurality of functional groups in the molecule to increase a viscosity, and
   molding the mixture after increasing the viscosity;
   wherein the powder of polymer (A) has an average particle diameter of from 2 to 200 μm,
   wherein the vinyl ester monomer (B) is a vinyl carboxylate monomer (B1),
   wherein the vinyl ester monomer (B) has two or more vinyl groups in the molecule,
   wherein in a spreading test comprising sandwiching 1 mL of the mixture obtained by mixing between glass plates and applying a load of 100 g, where a diameter of the mixture spread after completion of the test is 30 mm, the time from mixing of the components (A) and (B) to start of the load application is from 3 to 8 minutes,
   wherein the mixture is installed in an oral cavity while being in a viscous fluid state, and the mixture changes into an elastomer, and
   wherein the molded article is selected from the group consisting of a tissue conditioner, a functional impression material, and a lining material.

2. The process for producing a molded article according to claim 1, wherein the polymer (A) is a poly(alkyl(meth)acrylate) (A1).

3. The process for producing a molded article according to claim 1, further comprising adding and mixing a polymerization initiator (C) to increase the viscosity.

4. The process for producing a molded article according to claim 1, wherein when the molded article is immersed in water at 37° C., a Shore C hardness (H7) measured seven days after start of immersion is from 0.8 to 1.2 times a Shore C hardness (H) measured one day after start of immersion.

5. The process for producing a molded article according to claim 1, further comprising performing a polymerization reaction after molding.

6. The process for producing a molded article according to claim 1, wherein the vinyl carboxylate monomer (B1) is at least one monomer selected from the group consisting of divinyl oxalate, divinyl malonate, divinyl succinate, divinyl glutarate, divinyl adipate, divinyl azelate, divinyl suberate, divinyl sebacate, divinyl maleate, divinyl fumarate, divinyl phthalate, divinyl isophthalate, divinyl terephthalate, trivinyl hemimellitate, trivinyl trimellitate and trivinyl trimesate.

\* \* \* \* \*